United States Patent [19]
Watanabe et al.

[11] Patent Number: 5,460,814
[45] Date of Patent: Oct. 24, 1995

[54] FERMENTATION BROTH AND MICROORGANISMS WHICH PRODUCE THEM

[75] Inventors: Tsuneo Watanabe, Tsukuba; Takeshi Yasumoto, Sendai; Michio Murata, Itabashi; Michito Tagawa, Minamisaitama; Hiroyuki Narushima, Minamisaitama; Takashi Furusato, Minamisaitama; Masao Kuwahara, Minamisaitama; Masami Hanaue, Minamisaitama; Tatsuya Seki, Funabashi, all of Japan

[73] Assignee: Nissan Chemical Industries, Ltd., Tokyo, Japan

[21] Appl. No.: 228,712

[22] Filed: Apr. 18, 1994

Related U.S. Application Data

[62] Division of Ser. No. 100,171, Aug. 2, 1993, Pat. No. 5,346,919.

[30] Foreign Application Priority Data

Aug. 3, 1992 [JP] Japan .................. 4-206690

[51] Int. Cl.$^6$ .................. C12N 1/16; C12P 1/02
[52] U.S. Cl. .................. 424/122; 435/119; 435/255.1
[58] Field of Search .................. 435/255.1, 119; 424/122

[56] References Cited

FOREIGN PATENT DOCUMENTS 54-086693  7/1979  Japan .
62-040292  7/1987  Japan .

OTHER PUBLICATIONS

Abstract No. 140553a, *Chemical Abstracts*, vol. 82, No. 21, 26 May 1975 [sic, Jun. 2, 1975], Columbus, Ohio, U.S. and Dror, M. et al., *J. Polym. Sci., Polym. Chem. Ed.*, vol. 13, No. 1, 1975, pp. 171–187.

*Primary Examiner*—Bernard Dentz
*Attorney, Agent, or Firm*—Oliff & Berridge

[57] ABSTRACT

The present invention relates to the compound A of the formula (A), the related compound B, carboxylic acid derived from acid anhydride group of these compounds and esters and salts thereof, microorganisms for producing the compounds, methods for producing the compounds A and/or B by using the microorganisms, and a treated or untreated fermentation broth obtained by culturing strains belonging to genus Zopfiella or *Zopfiella curvata* No. 37-3 strain.

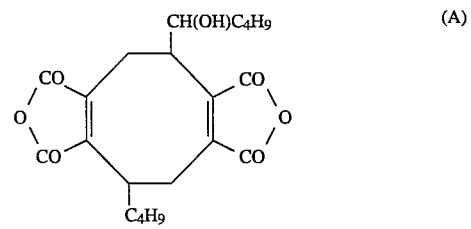

The present invention provides the compounds A and B, derivatives thereof, and treated or untreated fermentation broth obtained by culturing the strains belonging to genus Zopfiella or *Zopfiella curvata* No. 37-3 strain, which show an excellent activities as antifungal agent and anti-thrombotic agent.

7 Claims, 6 Drawing Sheets

FERMENTATION BROTH AND MICROORGANISMS WHICH PRODUCE THEM

This is a Division of application Ser. No. 08/100,171 filed Aug. 2, 1993, now U.S. Pat. No. 5,346,919.

BACKGROUND OF THE INVENTION

1. Field of the Invention

The present invention relates to novel compounds A and/or B, microorganisms which produce them and cultivated products thereof, and methods for producing the novel compounds by the microorganisms, as well as uses thereof. More particularly, it relates to the compounds A and B which exhibit antibacterial activity against various filamentous bacteria (mold fungi) and an activity for inhibiting platelet aggregation as well as to a microorganism capable of producing them, more particularly *Zopfiella curvata* No. 37-3 strain, a treated or untreated fermentation broth obtained by culturing strains belonging to the genus *Zopfiella curvata* or the *Zopfiella curvata* No. 37-3 strain, and a method for the production thereof by which a microorganism belonging to the genus *Zopfiella curvata* and capable of producing the compounds A and/or B is cultured and the compounds are collected, as well as to an antifungal agent, an agent for the control of plant diseases and an anti-thrombotic agent which contain any one of them as an active ingredient.

DESCRIPTION OF THE PRIOR ART

The existence of a substance which exhibits antibacterial activity against various filamentous bacteria (mold fungi) and has an activity as an anti-thrombotic agent, such as the one belonging to the genus *Zopfiella* disclosed by the present invention, has not been demonstrated.

There are problems of resistance against the existing antifungal agents, and the development is being sought of an antifungal agent which exhibits an effect against various filamentous bacteria (mold fungi). Moreover, the development of a novel agent having inhibitory activity of platelet aggregation mentioned below has been expected.

It is known that platelet aggregation plays an important role for thrombus formation in connection with a disease state. Various thrombotic disease caused by thrombus formation mainly include cerebral thrombosis, pulmonal thrombosis, myocardial infarction, angina pectoris, obstruction of peripheral artery and the like, and all of these diseases require development for useful drugs. As a prophylactic or therapeutic drug, an anti-thrombotic agent having an inhibitory activity of platelet aggregation draws public attention. Heretofore, the effect of aspirin has been widely studied, and more recently ticlopidine and cilostazol have been clinically developed. However, a more strongly effective drug is demanded in respect of its effect.

In addition to the above-mentioned various thrombotic diseases, there are enumerated various diseases in relation to platelets. Examples for these diseases, include nephritis, cancer cell metastasis and the like, and recently various studies have been conducted with regard to prophylactic or therapeutic effects for these diseases achieved mainly by an anti-thrombotic agent having an activity for controlling platelet function. ("Journal of Royal College of Physicians", Vol. 7, No. 1, pp. 5–18, 1972; "Japan Clinics (Nihon Rinsho)", Vol. 4, No. 6, pp. 130–136, 1988 and Anticancer Research, Vol. 6, pp. 543–548, 1986)

SUMMARY OF THE INVENTION

The present inventors, as a result of diverse investigation regarding the metabolic products of microorganisms, have discovered that a strain belonging to the genus *Zopfiella* produces a novel compound A which has antibacterial activity against various filamentous bacteria (mold fungi) activity as an anti-thrombotic agent and has an activity as an anti-thrombotic agent, and, moreover, produces a novel compound A which has an 8-membered cyclic structure and is represented by the following structure formula (A) and a novel compound B which has the physicochemical properties mentioned below. Furthermore, they found out that a treated or untreated fermentation broth obtained by culturing the strains belonging to Zopfiella have the same activities.

(A)

The present invention has been completed on the basis of the above-mentioned discovery.

DETAILED DESCRIPTION OF THE INVENTION

The above-mentioned novel compound A may be obtained by culturing the compound A-producing microorganism belonging to the genus *Zopfiella* to produce and accumulate the compound A, and harvesting the compound A from the culture. The compound A disclosed by the present invention is a substance newly discovered in nature.

A microorganism belonging to the genus *Zopfiella* and capable of producing the novel compound A may be used. An example of the compound A-producing bacteria belonging to the genus *Zopfiella* which may be used according to the present invention is *Zopfiella curvata* No. 37-3 strain (hereinafter referred to as "No. 37-3 strain") which was newly separated from soil in Saitama Prefecture of Japan by the present inventors. Other examples thereof include *Zopfiella latipes, Zopfiella longicaudata, Zopfiella lundqvistii, Zopfiella marina, Zopfiella matsushimae, Zopfiella pilifera*, etc. The bacteriological properties of No. 37-3 strain are given below.

1. Morphology

The ascocarps are superficial, and largely scattered. They are blackish-brown, opaque and globular. Their diameter is 210 μm–324 μm. Setae adhere to the ascocarps, with generally 4–6 thick diaphragms present. The setae appear dark brown. Their length is 195 μm–325 μm. The bases of the setae are 4.5 μm–6.3 μm in width. The shell walls of the ascocarps are seam-shaped, and are easily divided into hexagonal tissues.

The asci are globular and 180 μm–216 μm in diameter. They often form pods, and the length of the pod sections is 8 μm–13 μm. Their width is 3 μm–8 μm. The asci comprise 8 cells.

The ascospores are 13.5 μm–19.8 μm in length and 5 μm–5.8 μm in width, and mainly exhibit a curved form. The two upper layer cells are light brown to olive when young, later appearing brown.

The one lower layer cell is colorless. This colorless cell is readily destroyed, and the destroyed ascospores are bicellular, exhibiting a sheathed form.

Based on the above-properties, No. 37-3 strain is identified as a strain belonging to the genus *Zopfiella curvata*, of filamentous bacteria (mold fungi).

The present strain has been deposited at Patent Microorganism Depository, National Institute of Bioscience and Human-technology, Agency of Industrial Science and Technology of the Ministry of International Trade and Industry in Japan (the address of said Institute: 1-3 Higashi 1-chome, Tsukuba-shi, Ibaraki-Ken, Japan) under the name *Zopfiella curvata* No. 37-3, as No. 13067 (FERM P-13067) and International Deposition No. BP-4369 under the Budapest Treaty.

The ability of *Zopfiella curvata* No. 37-3 to be used according to the present invention for producing the compound A and/or compound B may be augmented by a conventionally used mutation process, e.g., irradiation with ultraviolet rays, $^{60}$Co, etc., treatment with a mutagenic agent such as nitrous acid, N-methyl-N'-nitro-N-nitrosoguanidine (NTG), or the like, transduction, transformation, cell fusion, etc.

To produce the novel compound A and/or compound B according to the present invention, a microorganism belonging to the genus Zopfiella and capable of producing the novel compound A and/or compound B, or a microorganism whose ability to produce the novel compound A and/or compound B has been augmented by the above-mentioned treatment, may be cultured in a culture medium, and the novel compound A and/or compound B may be produced and accumulated in the culture and then harvested. Any microorganism belonging to the genus Zopfiella and producing the novel compound A and/or compound B may be used.

The method of culturing generally follows the methods of culturing filamentous bacteria (mold fungi), and usually submerged culturing in a liquid is effective. The medium to be used for the culturing may be one which contains a nutrient source which can be utilized by the strain 37-3.

The nutrient source to be used may be a well known one which has been used for the culturing of filamentous bacteria (mold fungi) in the past, for example, as a carbon source, glucose, galactose, mannitol, dextrin, starch, starch syrup, soybean oil, etc. may be used either alone or in admixture.

As an inorganic or organic nitrogen source, ammonium chloride, ammonium sulfate, urea, ammonium nitrate, peptone, beef extract, yeast extract, corn steep liquor, soybean cake, oatmeal, casamino acid, bacto soytone, soluble vegetable protein, etc. may be used either alone or in admixture.

In addition, inorganic salts such as sodium chloride, magnesium sulfate, copper sulfate, zinc sulfate, manganese chloride, calcium carbonate and phosphates may be added as necessary, either alone or in admixture, and also organic substances, such as nucleic acids, amino acids, vitamins and the like or inorganic substances, may be added as appropriate to accelerate the growth of the bacterium or the production of the novel compounds A and/or B.

If considerable foaming occurs in the culture, then a vegetable oil such as soybean oil or a petroleum antifoaming agent such as silicone, may be appropriately added.

The culturing temperature is preferably 20°–28° C., and the pH of the culture is preferably adjusted to 5.8–8.0. With a liquid rotatory shaking culture, it is normally preferable to carry out the culturing for 8–16 days. Also, a standing culture may be used. The respective optimum culturing conditions may be selected to be suitable for the properties of the producing strain used and the method of culturing.

It is possible to accumulate the present compounds in cells or out of cells by the selection of these culture conditions, whereby improving productability.

For the purification of the compounds A and/or B and isolation thereof from the culture after completion of the culturing, conventional methods of separation and purification for the isolation of microorganism metabolites from their cultures are used. That is, by using procedures including concentration under reduced pressure, lyophilization, extraction with an organic solvent, for example, extraction with butanol, methanol, ethanol, propanol, acetone, ethyl acetate, chloroform, benzene or the like; treatment with an ion-exchanger, for example, a cation exchange resin, anion exchange resin, or the like; or treatment with a macroporous, nonionic adsorption resin, or chromatography using an adsorbing agent such as active carbon, silicic acid, silica gel, alumina, etc.; high performance liquid chromatography (HPLC) or gel filtration chromatography using a Sephadex LH-20 or the like; or crystallization, recrystallization, etc., either alone or in combination in the order desired, or repeatedly, the novel compound A and/or compound B may be separated, purified and harvested.

The compound A of the present invention has the structure of an acid anhydride diketofuran, but depending on the difference in the conditions of extraction, dicarboxylic acid or tetracarboxylic acid, or ester derivative thereof or salt derivative thereof in which one or two diketofuran rings are cleaved. The ester derivative is esters of alcohol having 1 to 4 carbon atoms such as methyl, ethyl, propyl or butyl ester. The salt derivative is alkaline metal salt or alkaline earth metal salt such as sodium salt, potassium salt, calcium salt or ammonium salt. There may be combinations of any two or three of the carboxylic acid, the ester, the salt and the acid anhydride. These compounds are included in the present invention.

In a case that the compound B has a diketofuran structure, in similarity with the compound A, carboxylic acid derived from the acid anhydride group and ester or salt derived therefrom are included in the present compounds. In a case of the compound B having carboxylic acid group, ester and salt thereof is also included in the range of the present compounds in similarity with the compound A. Moreover, optical isomers of the compounds A and B are included in the range of the present invention.

The thus obtained novel compounds A and/or B exhibits activity against various filamentous bacteria (mold fungi), and may be effectively used as an antifungal agent in medicines, for animals, in agricultural chemicals, in foods and for industrial use, as well as an anti-thrombotic agent.

Specifically, the novel compounds A and/or B according to the present invention exhibit activity against plant pathogenic microbes which are seriously harmful from an agricultural point of view such as, for example, *Pythium debaryanum, Phytophthora infestans, Sclerotinia sclerotiorum, Sclerotinia cinerea, Venturia inaequalis, Septoria nodorum, Diaporthe citri, Pyrenophora teres, Botrytis cinerea, Pyricularia oryzae, Colletotrichum lagenarium, Pseudocercosporella herpotrichoides, Rhynchosporium secalis, Alternaria mali, Fusarium oxysporum, Rhizoctonia solani, Rhizoctonia solani,* and microorganisms which are seriously harmful from a medical or industrial point of view, such as *Aspergillus nigar, Aspergillus fumigatus, Trichophyton mentagrophytes, Trichophyton rubrum, Penicillium citrinum, Candida albicans, Saccharomyces cerevisiae,* etc.

The filtered liquid and its concentrated product which are prepared by removing cells of a culture liquid of using strain belonging to Zopfiella or *Zopfiella curvata* No. 37-3 under the substantially same conditions as these of obtaining the compound A, and solvate-extracts of the cells are called as a treated or untreated fermentation broth obtained by culturing strains belonging to genus Zopfiella or the *Zopfiella curvata* No. 37-3. Solvents used for the extraction are organic solvents such as methanol, ethanol, propanol, butanol, acetone, ethyl acetate, chloroform, benzene, etc.

The treated or untreated fermentation broth obtained by culturing the strains belonging to Zopfiella and the *Zopfiella curvata* No. 37-3 strain exhibit the same activities of the compound A and/or compound B. Hereinafter, all of the compound A, the compound B, a treated or untreated fermentation broth obtained by culturing strains belonging to genus Zopfiella and the *Zopfiella curvata* No. 37-3 are referred to as "the present compounds".

When using the novel compounds according to the present invention as an antibacterial agent for agricultural and horticultural use, any carrier may be used which does not inhibit the activity of the present compounds, including, for example, a solid carrier such as clay, talc, bentonite, diatomaceous earth, etc. or a liquid carrier such as water, an alcohol (methanol, ethanol, etc.), an aromatic hydrocarbon (benzene, toluene, xylene, etc.), a chlorinated hydrocarbon, an ether, a ketone, an ester (ethyl acetate, etc.), an acid amide (dimethylformamide, etc.), or the like, and if desired an emulsifier, dispersing agent, suspending agent, penetrating agent, spreader, stabilizer or the like may be added thereto to provide any desired formulation of the present compounds, such as a liquid formulation, oil solution, emulsifiable concentrates, wettable powders, dusts, granules, flowables, etc.

In addition, as required it may be used in admixture with an herbicide, a fungicide, an insecticide, a plant growth regulator, a synergist, fertilizer, or the like when its formulation is made or sprayed. The dosage of the present compounds used will differ depending on the situation, the time of use, the method of use, the target disease, the plant being cultivated, etc., but generally the amount of the effective ingredient is appropriate on the order of 5 g–50 kg per hectare.

On the other hand, when the novel present compounds are used as an antifungal agent for medicinal use, it may be applied to the affected area in the form of, for example, a liquid liniment, gel or ointment, to achieve the purpose of the treatment.

Moreover, as the manner of administration of the present compounds as an anti-thrombotic agent, there may be mentioned a parenteral administration by injection (subcutaneous, intravenous, intramuscular or intraperitoneal injection), an ointment, a suppository or an aerosol, or an oral administration in the form of tablets, capsules, granules, pills, sirups, liquids, emulsions or suspensions.

The above pharmacological composition contains the present compounds in an mount of from about 0.1%–99.5% by weight, preferably from about 0.5%–95% by weight, based on the total weight of the composition.

To the present compounds or to the compositions containing the present compounds, other pharmacologically active compounds may be incorporated. Further, the compositions of the present invention may contain a plurality of the present compounds.

The clinical dose of the present compounds varies depending upon the age, the body weight, the sensitivity or the sympton, etc. of the patient. However, the effective daily dose is usually from 0.003 g–1.5 g, preferably from 0.01 g–0.6 g, for an adult. If necessary, however, an amount outside the above range may be employed.

The present compounds may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as sirups, gum arabic, gelatin, sorbitol, tragacanth gum, methyl cellulose or polyvinylpyrrolidone; a disintegrant such as starch, carboxymethyl cellulose or its calcium salt, crystal cellulose powder or polyethylene glycol; a lubricant such as talc, magnesium or calcium stearate, silica, sodium laurate or glycerol.

The injections, solutions, emulsions, suspensions, sirups or aerosols, may be prepared by using a solvent for the active ingredient such as water, ethyl alcohol, isopropyl alcohol, propylene glycol, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl cellulose, a cellulose derivative such as methyl cellulose, or natural rubber such as tragacanth gum or gum arabic; or a preservative such as a paraoxy benzoic acid ester, benzalkonium chloride or a salt of sorbic acid. Likewise, ointments which are percutaneously absorbable preparations may be prepared by using, e.g., white vaseline, liquid paraffin, a higher alcohol, Macrogol ointment, hydrophilic ointment or hydrogel base. The suppositories may be prepared by using, e.g., cocoa butter, polyethylene glycol, lanolin, fatty acid triglyceride, coconut oil or polysorbate.

EXAMPLES

A more detailed description of the present invention is provided below with reference to the Examples, but the Examples do not restrict in any way the scope of the present invention.

Example 1

*Zopfiella curvata* No. 37-3 strain was cultured at 25° C. for 5 days in a liquid culture medium (pH 7.0) containing PD (potato dextrose, product of Difco Co.) as the seed culture, and the resulting culture solution was inoculated into a fermentation culture medium, i.e., a medium (pH 7.0) prepared by adding 0.1% polypeptone, 0.1% yeast extract and 10% (v/v %) tomato juice (containing salt, product of Kagome, Inc.) to a PD (potato dextrose) culture medium (product of Difco Co.), and the mixture was subjected to rotatory culturing (140 rpm) at 25° C. for 12 days.

The resulting culture solution was filtered to remove the cells, and then the filtrate from the culture was adjusted to pH 3 using 2N hydrochloric acid. To 1.5 liters of the filtrate was added ethyl acetate for extraction, to obtain an ethyl acetate-extracted fraction. The ethyl acetate-extracted fraction was concentrated under reduced pressure, and the solvent was removed, after which the precipitate was dissolved in a small amount of benzene:ethyl acetate:acetic acid (80:1:2), charged into a silica gel column which had been previously equilibrated with the same type of solvent, and then eluted by the same type of solvent. The active fractions were concentrated and, after the solvent was removed, the solution was applied to a Sephadex LH-20 column chromatography which had been previously equilibrated with benzene and eluted by benzene:acetic acid (40:1) to obtain fractions containing the compounds A and B, respectively. After the fraction containing the compound A was concentrated, a single peak portion was collected by conducting HPLC under the conditions of a device: Shimazu LC-5A manufactured by Shimazu Manufacturing Co., Ltd. in Japan; column: Inertsil ODS-2 φ 4.6 mm×250 mm (manufactured by GL Sciences, Ltd.); developing solvent:acetonitrile - water (80:20 v/v %), flow rate: 1.0 ml/min.; temperature: 25° C.; and determination: UV 254 nm, to obtain about 40 mg of the compound A. Similarly, after the fraction containing the compound B was concentrated, HPLC having the above conditions was conducted to collect a single peak portion so as to obtain about 10 mg of the compound B. The activities of the compounds A and B in the culture and in the crude fractions was determined by the paper disk method using *Botrytis cinerea*.

The thus obtained compounds A and B are novel substances.

The compound A which possesses the following physicochemical properties.

1. Molecular weight: 390
2. Molecular formula: $C_{21}H_2O_7$ (Detection by FAB Mass spectrum, $(M+H)^+=391$. M/Z= 391.1741 was obtained by precision mass measurement. Also, elemental analysis confirmed the absence of nitrogen. From the above results, a molecular weight of 390 and a molecular formula of $C_{21}H_2O_7$ were deduced.

Figure 1:
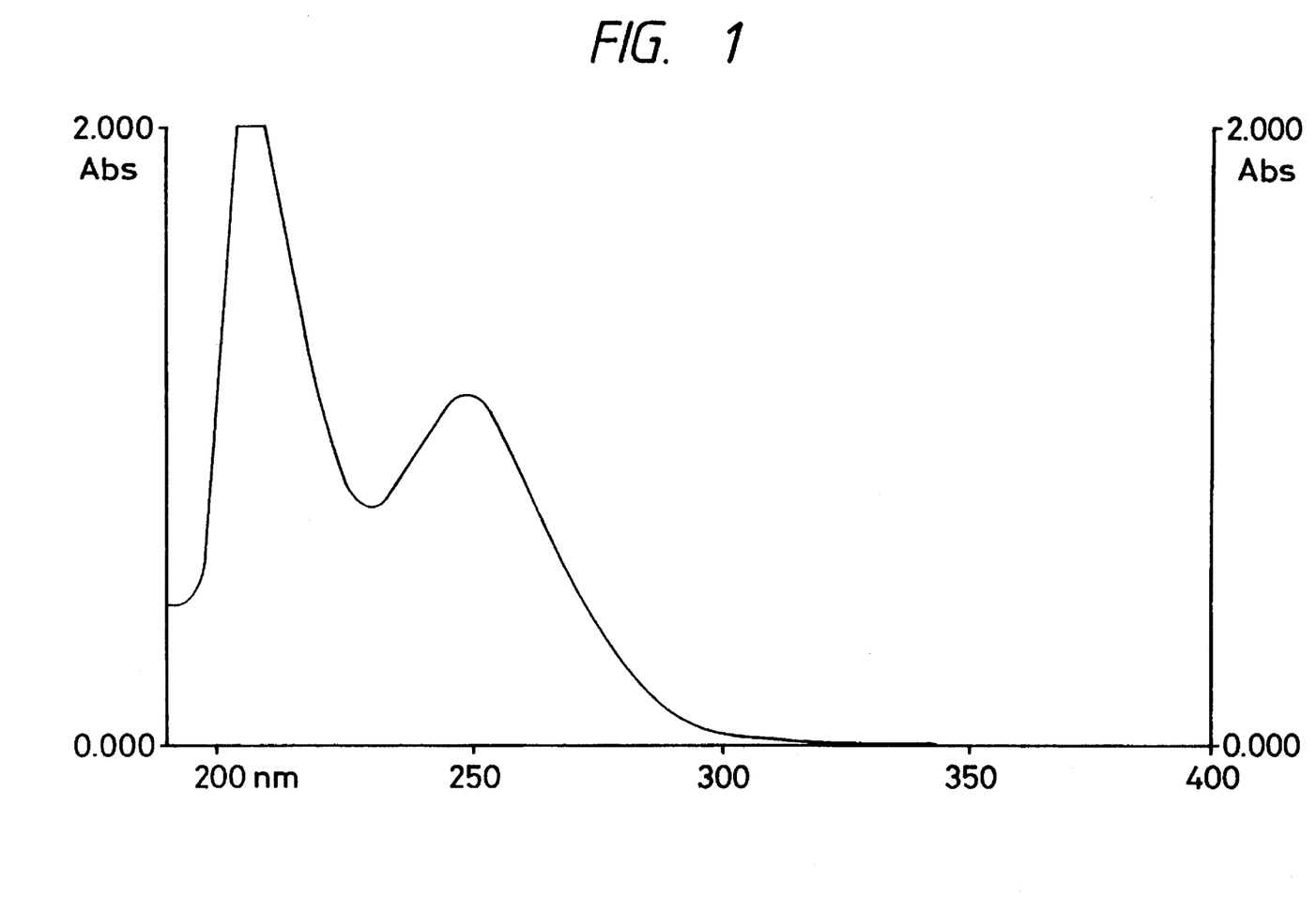
FIG. 1 shows an ultraviolet absorption spectrum of the novel compound A.
Figure 2:
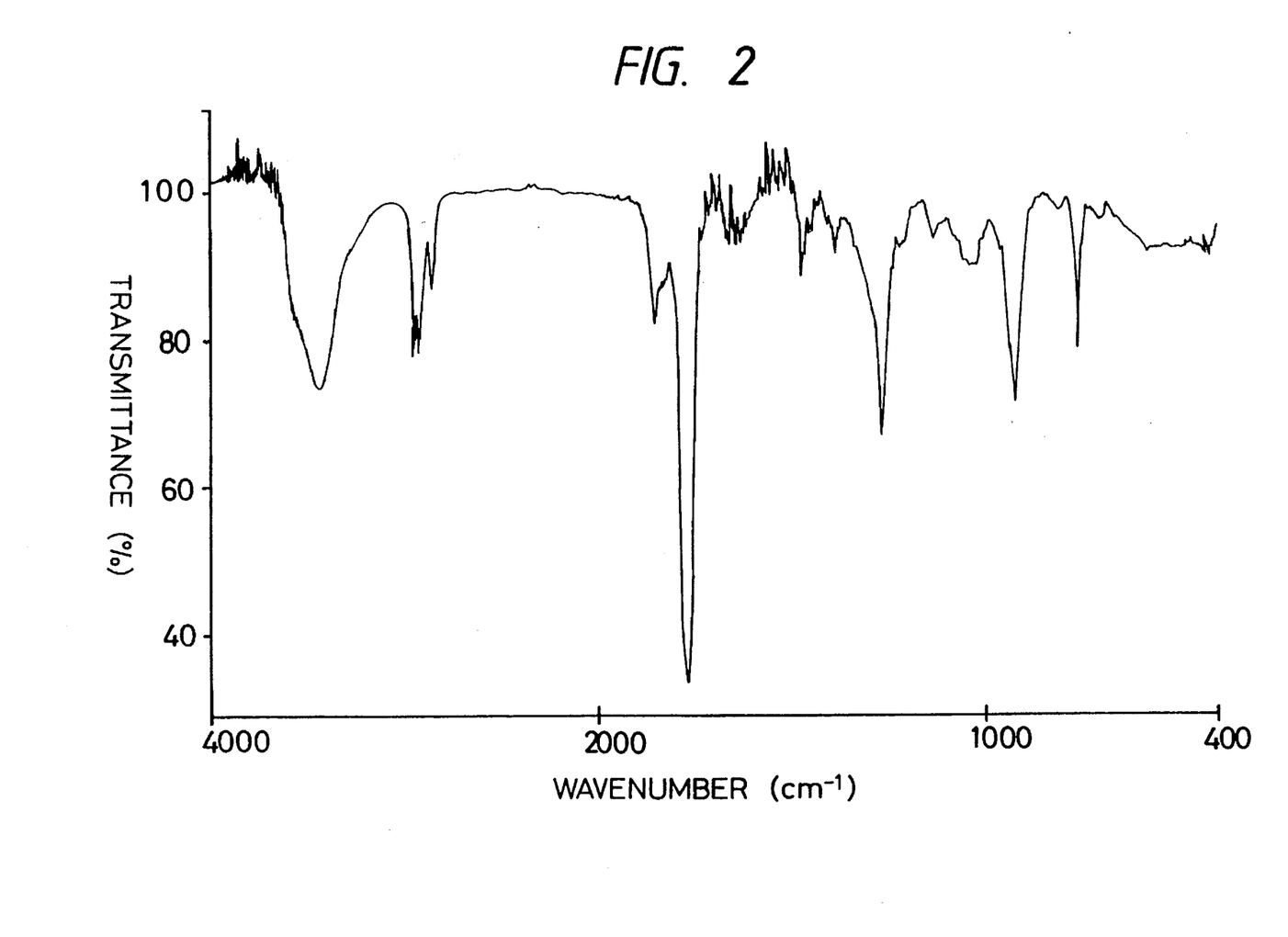
FIG. 2 shows an infrared absorption spectrum of the novel compound A.
Figure 3:
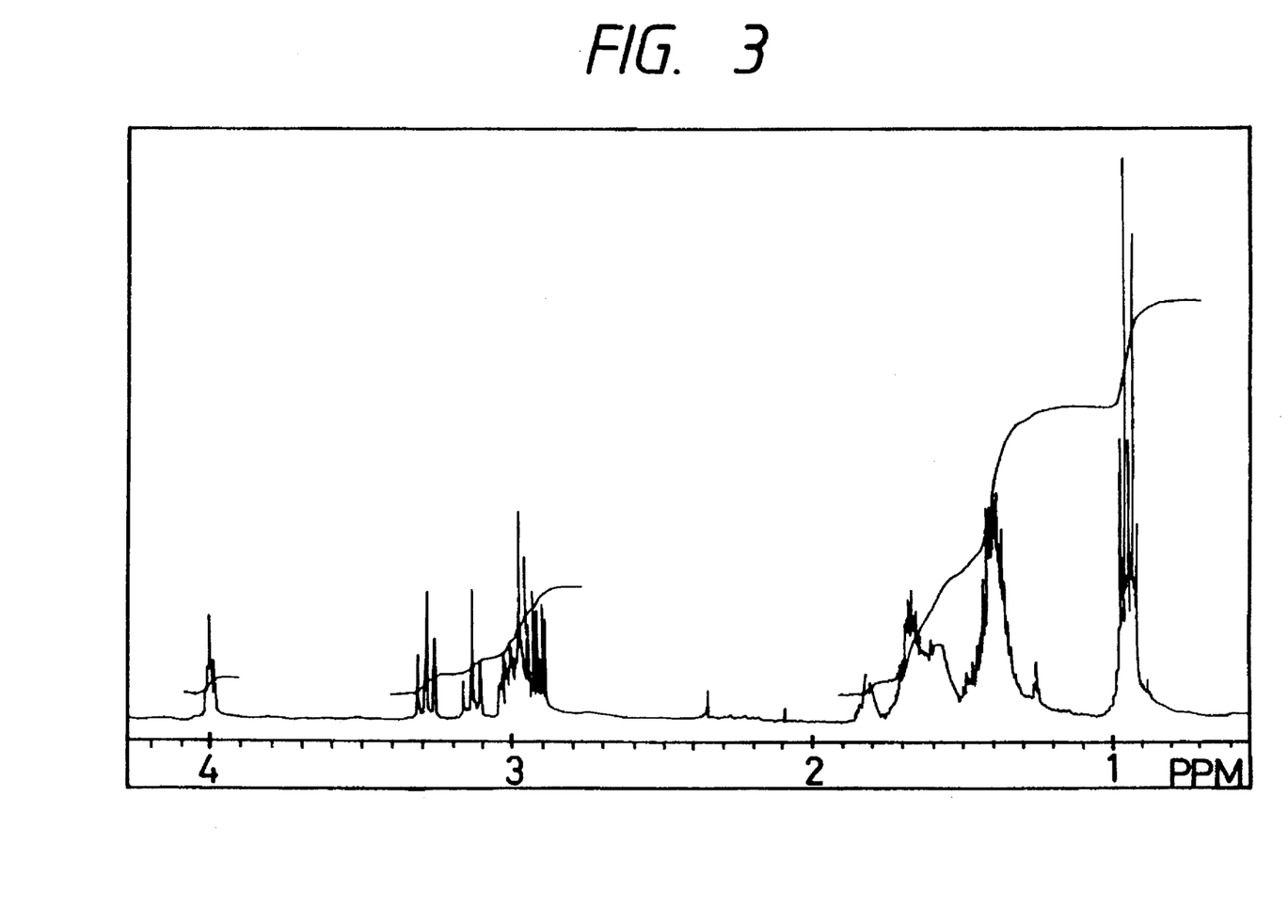
FIG. 3 shows a proton nuclear magnetic resonance spectrum of the novel compound A.

3. Specific optical rotation: $[\alpha]_D^{23}=-76.8°$ (C=0.42, methanol)
4. Color and form of substance: White powder
5. Ultraviolet absorption spectrum: $\lambda_{max}^{MeOH}=250$ nm ($\epsilon$ 6300) Shown in FIG. 1
6. Infrared absorption spectrum: $v_{max}^{KBr}=3300-3500$, 2960, 2935, 1850, 1770, 1260, 915, 750 $cm^{-1}$ Shown in FIG. 2.
7. Solubility in solvents: readily soluble in chloroform, ethyl acetate, methanol; sparingly soluble in water
8. Proton nuclear magnetic resonance spectrum The hydrogen nuclear magnetic resonance spectrum measured in heavy chloroform is shown in FIG. 3.

Figure 4:
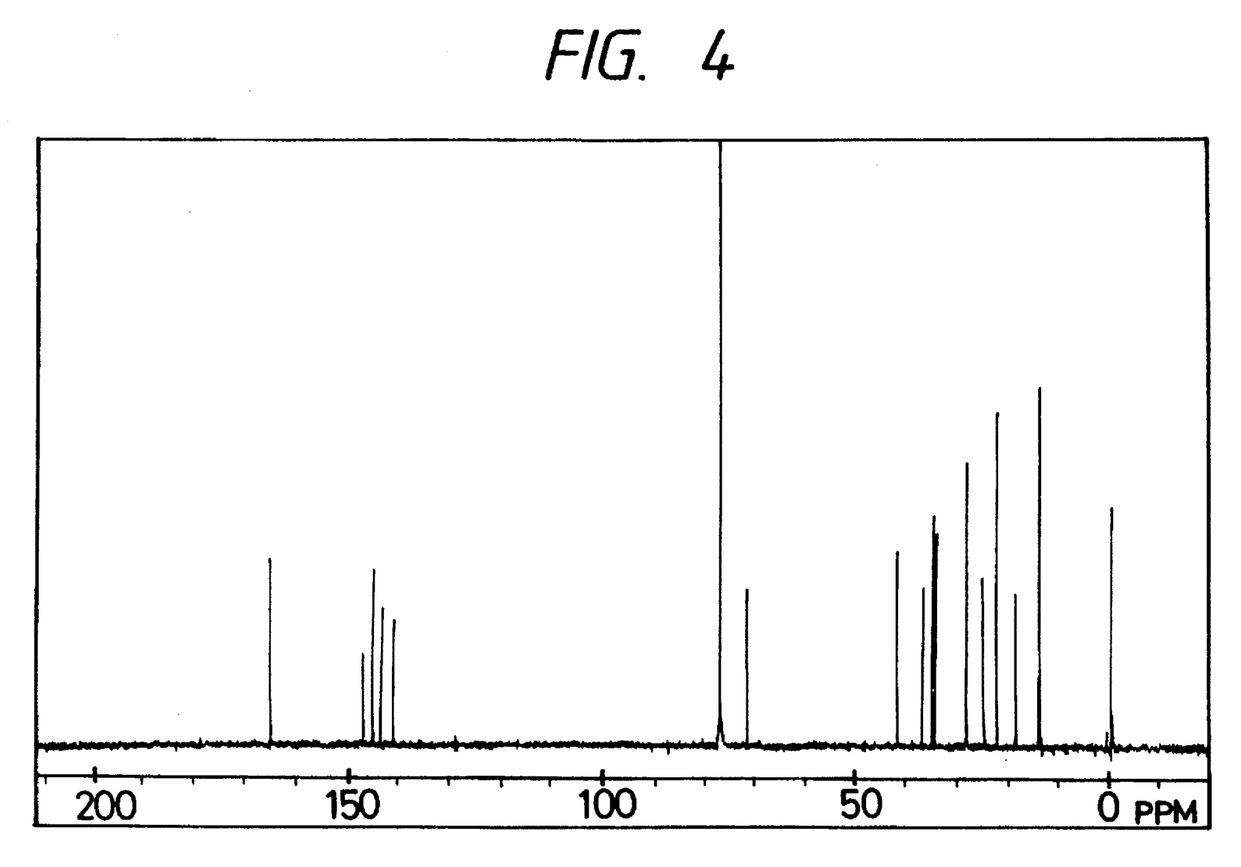
FIG. 4 shows $^{13}C$ nuclear magnetic resonance spectrum of the compound A.

9. $^{13}C$ nuclear magnetic resonance spectrum ($CDCl_3$)

The carbon nuclear magnetic resonance spectrum measured in heavy chloroform is shown in FIG. 4. The chemical shifts (δ-values) are listed below.

13.8, 13.9, 18.5, 22.4, 22.4, 24.9, 28.1, 28.4, 34.1, 34.8, 36.5, 41.7, 71.6, 141.0, 143.3, 145.0, 147.3, 165.0, 165.1, 165.4, 165.5 ppm 10. Rf value: Silica gel thin-layer chromatography Keisel gel $60F_{254}$, Merck Co.)

0.35 in a solvent system of benzene:ethyl acetate:acetic acid (80:1:2 v/v %)

Furthermore, based on the above physicochemical properties and the results from spectral analysis, the chemical structure of the compound A was identified as Structural Formula (A) below.

The compound B possesses the following physicochemical properties.

Figure 5:
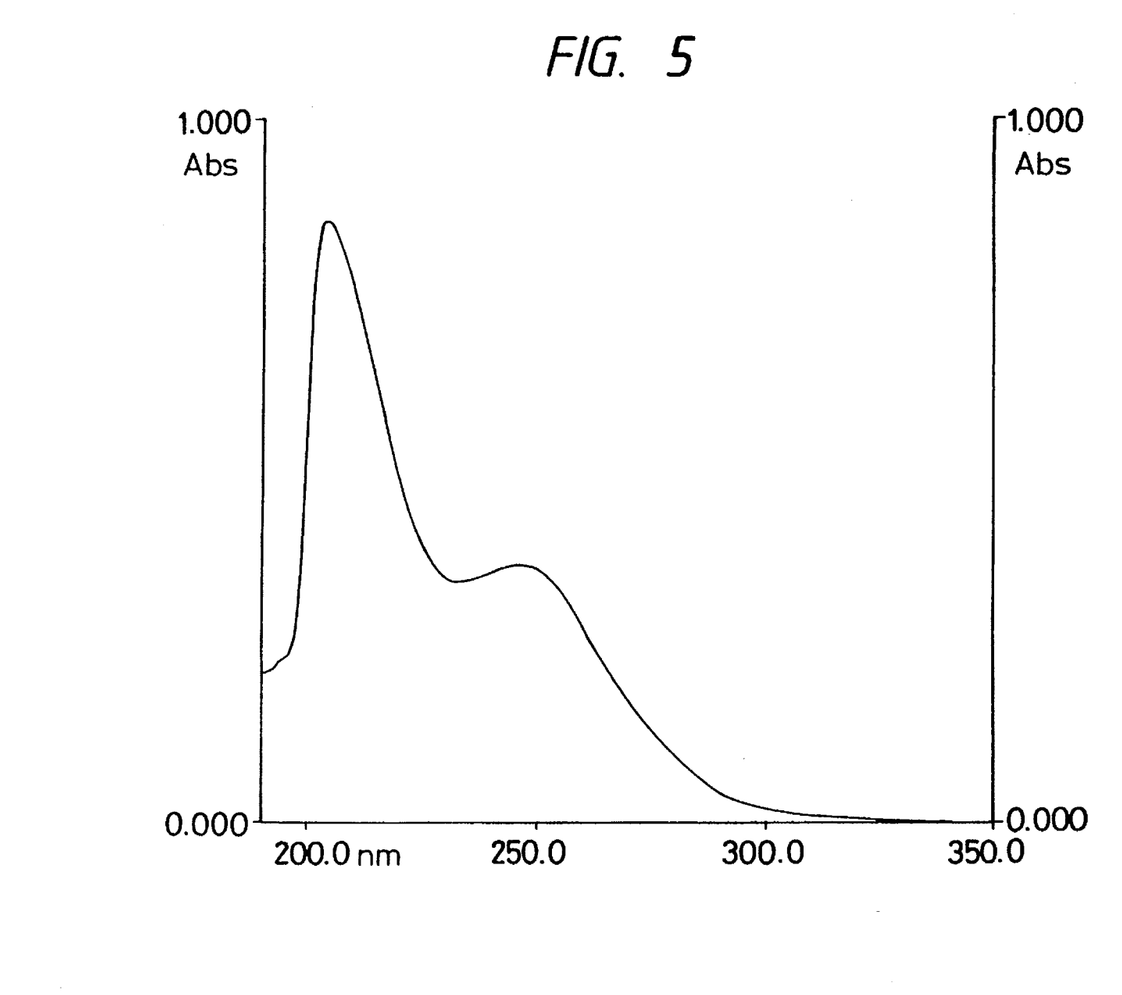
FIG. 5 shows an ultraviolet absorption spectrum of the novel compound B.
Figure 6:
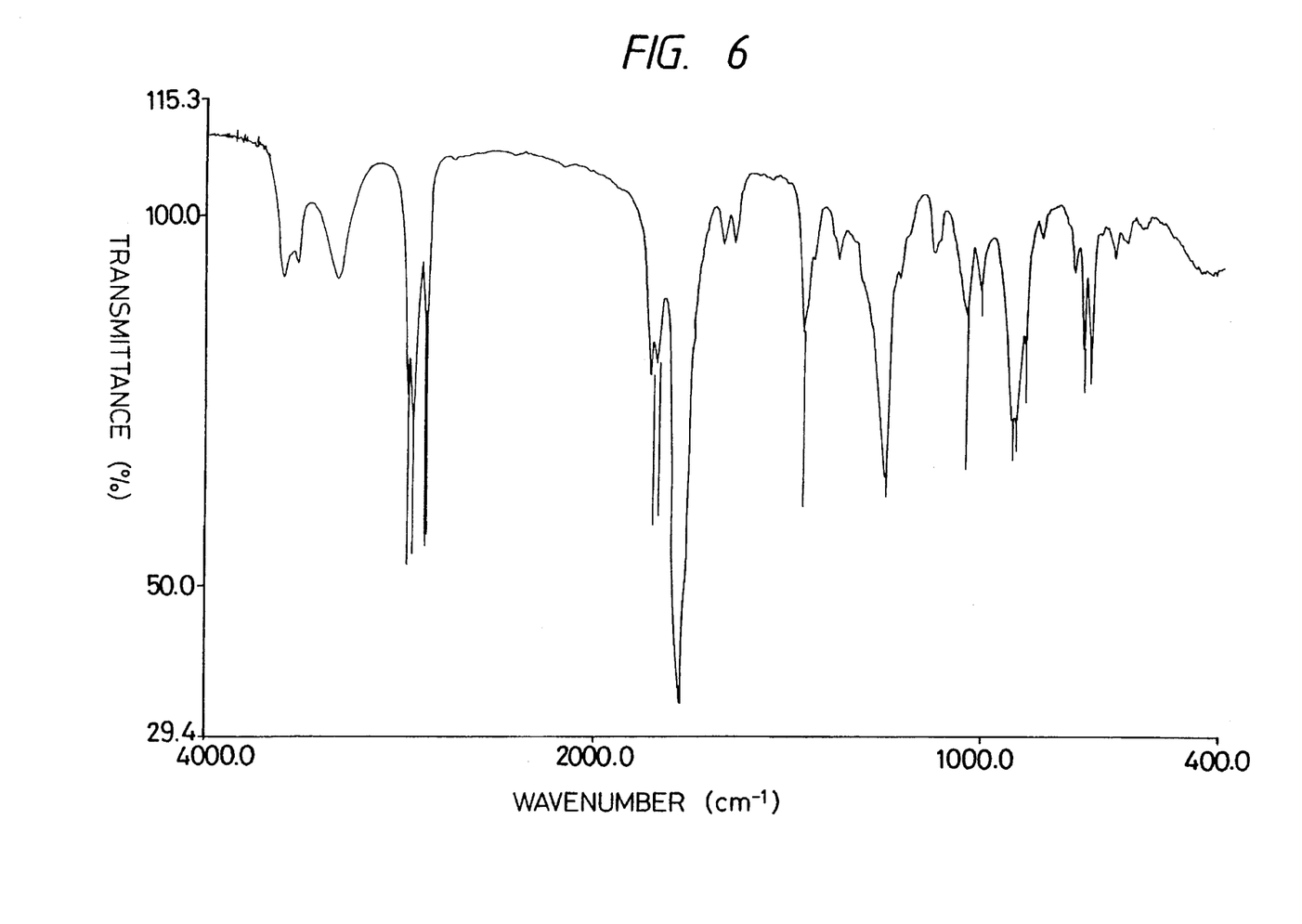
FIG. 6 shows an infrared absorption spectrum of the novel compound B.

1. Molecular weight: 404
2. Molecular formula: $C_{22}H_{28}O_7$
3. Color and form of substance: White powder
4. Ultraviolet absorption spectrum: $\lambda_{max}^{MeOH}=246$ nm ($\epsilon$ 6200) Shown in FIG. 5
5. Infrared absorption spectrum: $v_{max}^{KBr}=2960$, 2960, 2930, 2860, 1850, 1830, 1770, 1470, 1255, 930, 750, 735 $cm^{-1}$ Shown in FIG. 6.
6. Solubility in solvents: readily soluble in chloroform, ethyl acetate and methanol; sparingly soluble in water
7. $^{13}C$ nuclear magnetic resonance spectrum ($CDCl_3$)

The chemical shift (δ-value) measured in heavy chloroform is shown below.

δ(ppm): 13.9, 14.0, 22.4, 22.5, 22.6, 26.7, 27.4, 29.2, 31.5, 34.7, 35.0, 35.9, 41.9, 66.5, 143.9, 144.0, 144.4, 144.7, 164.1, 164.4, 165.2, 165.8

Example 2

Synthesis of Tetramethylester of the Compound A

Ten (10) mg of the compound A was dissolved in 30 ml of diethyl ether. Thirty (30) mg of silica gel was added to the solution and suspended. Diazomethane was introduced into the resulting solution and was reacted at 0° C.–10° C. for 20 min. The silica gel was filtered and the solvent was distilled off under reduced pressure to obtain 12 mg of oil. The obtained product was purified with HPLC to obtain 5 mg of tetramethyl ester of the compound A as an oil.

Ultraviolet absorption spectrum ($cm^{-1}$): 3600–3200, 2910, 2840, 1710

Mass spectrometry: 482 ($M^+$), 464, 451, 419, 364, 332, 304, 277, 276, 247, 217, 69

$H^1$-NMR δ(ppm, TMS): 3.746 (s, 3H), 3.730 (s, 3H), 3.726 (s, 3H), 3.719 (s, 3H)

Activity of the Compound A for Inhibiting the Growth Against Filamentous Bacteria (Mold Fungi)

An explanation will now be provided regarding the biological activity of the novel compound A. The compound A exhibits a strong growth-inhibiting effect against some filamentous bacteria (mold fungi). The measurement of the minimum growth inhibition concentration (MIC) was made following the agar plate dilution method using an agar medium containing the compound A.

The results are shown in Table 1.

TABLE 1

| Pathogenic bacterium | Minimum growth inhibition concentration (μg/ml) |
|---|---|
| Sclerotinia sclerotiorum | 1.56 |
| Sclerotinia cinerea | 3.13 |
| Botrytis cinerea | 0.78 |
| Rhynchosporium secalis | 1.56 |
| Aspergillus nigar | 3.13 |

Fungicidal Activity Against *Botrytis cinerea* by the Compound B

A mycelia disk had been prepared from the tip of a cell cluster of *Botrytis cinerea* cultured at 25° C. for 2 days in a PDA medium by using a 4 mm-diameter cork borer. The mycelid disk was placed at a central portion of a PDA medium. Then, paper disks (each 8 mm in diameter) applied with the compound B containing various concentrations were placed at distances equal from the center of the cell cluster to be cultured at 25° C. for 2 days. As a result, the compound B of the present invention inhibited the growth of mycelia of *Botrytis cinerea* at the concentration of 5 μg.

Examples will now be provided of formulations of antibacterial agents containing as an effective ingredient the present compounds, but they are not limitative to the scope of the invention. In the following examples of formulations, "parts" refers to "parts by weight".

Formulation Example 1

Emulsifiable Concentrates

| Present compound | 20 parts |
|---|---|
| Xylene | 55 parts |
| N,N-dimethylformamide | 20 parts |
| Sorpol 2680 | 5 parts |
| (A mixture of a nonionic surfactant and an anionic surfactant: trade name of Toho Chemical, Co., Ltd., Japan) | |

The above components are mixed intimately to produce an emulsifiable concentrate. When used, the above-mentioned emulsifiable concentrate diluted 50–20000-fold, and is dispersed for an amount of 5 g–50 kg of the effective ingredient per hectare.

Formulation Example 2

Wettable Powders

| Present compound | 25 parts |
|---|---|
| Zeeklite PFP | 66 parts |
| (A mixture of kaolinite and sericite: trade name of Zeeklite Mining Industries) | |
| Sorpol 5039 | 4 parts |
| (Anionic surfactant: trade name of Toho Chemical Co., Ltd.) | |
| Carplex #80 | 3 parts |
| (White carbon: trade name of Shionogi Seiyaku K.K., Japan) | |
| Calcium lignin sulfonate | 2 parts |

The above components are mixed intimately and ground together to produce a wettable powder. When used, the above mentioned wettable powder is diluted 50–20000-fold, and is dispersed for an amount of 5 g–50 kg of the effective ingredient per hectare.

Formulation Example 3

Oil Solution

| Present compound | 10 parts |
|---|---|
| Methylcellosolve | 90 parts |

The above components are mixed intimately to produce an oil solution. When used, the above mentioned oil solution is dispersed for an amount of 5 g–50 kg of the effective ingredient per hectare.

Formulation Example 4

Dusts

| Present compound | 3 parts |
|---|---|
| Carplex #80 | 0.5 parts |
| (White carbon: trade name of Shionogi Seiyaku K.K.) | |
| Clay | 95 parts |
| Diisopropyl phosphate | 1.5 parts |

The above components are mixed intimately and ground together to produce a dust. When used, the above mentioned powder is dispersed for an amount of 5 g–50 kg of the effective ingredient per hectare.

Formulation Example 5

Granules

| Present compound | 5 parts |
|---|---|
| Bentonite | 54 parts |
| Talc | 40 parts |
| Calcium lignin sulfonate | 1 part |

The above components are mixed intimately and ground together, a small amount of water is added thereto and the mixture is stirred, and granules are formed with an extrusion granulator and then dried to obtain granules. When used, the above mentioned granules are dispersed for an amount of 5 g–50 kg of the effective ingredient per hectare.

Formulation Example 6

Flowables

| | |
|---|---|
| Present compound | 25 parts |
| Sorpol 3353 | 10 parts |
| (Nonionic surfactant: trade name of Toho Chemical Co., Ltd.) | |
| Lunox 1000C | 0.5 part |
| (Anionic surfactant: trade name of Toho Chemical Co., Ltd.) | |
| 1% aqueous solution of xantham gum (Natural polymer) | 20 parts |
| Water | 44.5 parts |

All of the above mentioned components except for the effective ingredient (the present compound) are dissolved intimately, the present compound is added thereto, and the mixture is stirred well and then made into a wet grinding with a sand mill to obtain a flowable. When used, the above mentioned flowable is diluted to 50–20000-fold and dispersed for an amount of 5 g–50 kg of the effective ingredient per hectare.

Examples will now be provided of formulations of antibacterial agents for medicinal use, containing as an effective ingredient the present compounds, but they are not limitative to the scope of the present invention.

Formulation Example 7

Liquid Liniment

| | |
|---|---|
| Present compound | 3 parts |
| Diethanolamine | 10 parts |
| Ethanol | 87 parts |

Diethanolamine is added to a small amount of ethanol, and the mixture is stirred intimately to make a solution. The substance according to the present invention is added to the solution and stirred and dissolved therein, and ethanol is further added to obtain a liquid liniment.

Formulation Example 8

Ointment

| | |
|---|---|
| Present compound | 1 part |
| Diethanolamine | 3 parts |
| White vaseline | 86 parts |
| Stearic acid | 10 parts |

The white vaseline and stearic acid are heated and dissolved, and diethanolamine is added thereto to uniformity to make a solution. The compound according to the present invention is added to the solution and stirred and dissolved therein, and then the solution is allowed to solidify at room temperature to obtain a formulation.

The following is an explanation of a case where the present compounds are administered as an anti-thrombotic agent.

Formulation Example 9

Tablets

| | |
|---|---|
| Present compound | 10 g |
| Lactose | 20 g |
| Corn starch | 4 g |
| Corn starch (for paste) | 1 g |
| Magnesium stearate | 100 mg |
| CMC—Ca* | 7 g |
| Total | 42.1 g |

(*carboxymethylcellulose calcium)

The above components were mixed by a usual method and then tabletted to produce tablets each containing 50 mg of the active ingredient.

Formulation Example 10

Capsules

+TL,6 Present compound? +TR,24 10 g? +TL,27 ? Lactose20 gCrystal cellulose powder10 gMagnesium stearate1 g Total41 g The above components were mixed by a usual method and then packed in gelatin capsules to obtain a capsule containing 50 mg of the active ingredient.

Formulation Example 11

Soft capsules

| | |
|---|---|
| Present compound | 10 g |
| Corn oil | 35 g |
| Total | 45 g |

The above components were mixed and packed in soft gelatin capsules by a usual method.

Formulation Example 12

Ointment

| | |
|---|---|
| Present compound | 1.0 g |
| Olive oil | 20 g |
| White vaseline | 79 g |
| Total | 100 g |

The above components were mixed by a usual method to obtain an 1% ointment.

Formulation Example 13

Aerosol Suspension

| | |
|---|---|
| (A) | |
| Present compound | 0.25% |
| Isopropyl myristate | 0.10% |
| Ethanol | 26.40% |
| (B) | |

-continued

| Mixture of 60–40% of 1,2-dichloro-tetrafluoroethane and 1-chloropentafluoroethane | 73.25% |

The above components of (A) were mixed and the obtained mixed solution was put in a vessel equipped with a valve, and about 20° C. of the injecting agent of (B) was fed under pressure from the valve nozzle up to the gauge pressure of about 2.46–2.81 mg/cm$^2$ to obtain aerosol suspension.

A concrete explanation will now be provided regarding the usefulness of the novel compound A and the like, with reference to the following test examples. However, it is not limitative to the scope of the present invention.

Test Example 1

Test for Controlling Gray Mold (*Botrytis cinerea*) on Cucumber (Prevention Test)

Onto 1.5 leaf-stage cucumber (variety: Sagamihanjiro) which had been grown in a 7 cm-diameter pot was sprayed, using a spray gun, a drug solution produced by diluting an emulsifiable concentrate containing the present compound with water to the predetermined concentration, at 10 ml per pot.

On the following day, the first leaf on which was sprayed the drug solution was plucked off, and onto the surface of the leaf was inoculated a mycelia disk which had been prepared from the tip of a cell cluster of *Botrytis cinerea* cultured at 20° C. for 2 days in a PSA (potato sucrose agar) medium using a 4 mm-diameter cork borer. Then, the cucumber leaf was allowed to stand for 5 days at 20° C. in a moist chamber, the diameter of the diseased spots which formed were measured, and the degree of control was determined according to the following equation. Here, iprodion (trade name: Lobral) was used as a control preparation.

Preventive value = (1 – diameter of disease spots of drug-treated group/diameter of disease spots of untreated group) × 100

The test results are shown in Table 2.

TABLE 2

| Test Compound | Concentration of spraying (ppm) | Preventive value | Toxicity |
|---|---|---|---|
| Compound A | 100 | 100 | none |
| | 50 | 100 | none |
| | 25 | 100 | none |
| Substance* | 100 | 100 | none |
| | 50 | 100 | none |
| Iprodion | 100 | 100 | none |
| | 50 | 95 | none |
| | 25 | 25 | none |

*Substance which is prepared by concentrating and drying ethyl acetate-extracted fraction of Example 1

Test Example 2

Test for Controling Gray Mold (*Botrytis cinerea*) on Cucumber (Curative Test)

The first leaf was plucked off from 1.5 leaf-stage cucumber (variety: Sagamihanjiro) which had been grown in a 7 cm-diameter pot, and a mycelia disk of *Botrytis cinerea* was inoculated in the same manner as in the Experiment 1. Then, the cucumber leaf was allowed to stand for 2 days at 20° C. in a moist chamber, and when the disease spots reached approximately 10 cm in diameter, a drug solution produced by diluting an emulsion containing the present compound with water to the desired concentration was sprayed at 10 ml per leaf using a spray gun, and after drying in air the leaf was allowed to stand for 3 days at 20° C. in a moist chamber.

The lengths of the newly developed diseases spots were measured, and the preventive value was determined using the following equation.

+TL,3 Preventive value =? +TL,13 (1 – length of diseased spots of drug-? treated group/length of diseased spots of untreated group) × 100

The test results are shown in Table 3.

TABLE 3

| Test Compound | Concentration of spraying (ppm) | Preventive value |
|---|---|---|
| Compound A | 100 | 79 |
| | 50 | 73 |
| Substance* | 100 | 75 |
| of extract* | 50 | 70 |
| Iprodion | 100 | 75 |
| | 50 | 70 |

*Substance which is prepared by concentrating and drying ethyl acetate-extracted fraction of Example 1

Test Example 3

Test for Controling Cucumber Sclerotinia Rot (*Sclerotinia sclerotiorum*) (Prevention Test)

Onto 1.5 leaf-stage cucumber (variety: Sagamihanjiro) which had been grown in a 7 cm-diameter pot was sprayed, using a spray gun, a drug solution produced by diluting an emulsifiable concentrate containing the present compound with water to the predetermined concentration, at 10 ml per pot.

On the following day, the first leaf on which was sprayed the drug solution was plucked off, and onto the surface of the leaf was inoculated a mycelia disk which had been prepared from the tip of a cell cluster of *Sclerotinia sclerotiorum* cultured at 20° C. for 1 day in a PSA medium by using a 4 mm-diameter cork borer. Then, the cucumber leaf was allowed to stand for 3 days at 20° C. in a moist chamber, the diameter of the disease spots which formed were measured, and the preventive value was determined according to the following equation.

+TL,3 Preventive value =? +TL,13 (1 – diameter of diseased spots of drug-? treated group/diameter of disease spots of untreated group) × 100

The test results are shown in Table 4.

TABLE 4

| Test Compound | Concentration of spraying (ppm) | Preventive value | Toxicity |
|---|---|---|---|
| Present compound | 100 | 100 | none |
|  | 50 | 100 | none |
| Iprodion | 100 | 100 | none |
|  | 50 | 100 | none |

Test Example 4

Anti-platelet Aggregation Effect

Blood was collected from the abdominal artery of Hartley male guinea-pigs (weight: about 300 g) into a syringe containing 1/10 volume 3.8% sodium citrate. The blood thus obtained was subjected to a centrifugation at 160×g for 10 minutes at room temperature to obtain platelet rich plasma (PRP). Furthermore, the residue was subjected to a centrifugation at 1500×g for 15 minutes to obtain platelet poor plasma (PPP). The measurement was carried out by diluting PRP with PPP to 300000/mm$^3$. The measurement range of transmittance was adjusted to 0% in the case of PRP and to 100% in the case of PPP. Thereafter, a test compound dissolved in 100% dimethylsulfoxide (DMSO) was added to PRP (the final concentration of DMSO: 0.5%). After incubation at 37° C., 1000 rpm for 2 minutes, an aggregating agent was added to measure an aggregation curve. The anti-platelet aggregation effect of the test compound was expressed by a concentration (IC$_{50}$: μM) at which the aggregation of control was 50% inhibited. The aggregating agents used were ADP (the final concentration: 5 μM), collagen (the final concentration: 2 μg/ml) and U46619 (the final concentration: 0.5 μM). The measurement of platelet aggregation was carried out using NBS HEMA Tracer 601.

Result

| | IC$_{50}$ (μM) | | |
|---|---|---|---|
| | ADP | Collagen | U46619 |
| Compound A | 187 | 42 | 484 |

U46619: [structure with COOH and OH groups]

As mentioned above, according to the present invention novel compounds, a treated or untreated fermentation broth obtained by culturing strains belonging to Zopfiella and a treated or untreated fermentation broth obtained by culturing strains belonging to genus Zopfiella or *Zopfiella curvata* No. 37-3, and *Zopfiella curvata* No. 37-3 can be provided which exhibits an excellent effect as an antifungal agent and an anti-thrombotic agent.

What is claimed is:

1. An antifungal agent comprising untreated fermentation broth obtained by culturing strains belonging to species *Zopfiella curvata* as an effective ingredient.

2. An antifungal agent as claimed in claim 1, wherein the microbial strain belonging to species *Zopfiella curvata* is *Zopfiella curvata* No. 37-3.

3. An agent for control of plant diseases comprising fermentation broth obtained by culturing a microbial strain belonging to species *Zopfiella curvata* as an effective ingredient.

4. An agent for control of plant diseases as claimed in claim 3, wherein the microbial strain belonging to species *Zopfiella curvata* is *Zopfiella curvata* No. 37-3.

5. An anti-thrombotic agent comprising fermentation broth obtained by culturing a microbial strain belonging to species *Zopfiella curvata* as an effective ingredient.

6. An anti-thrombotic agent as claimed in claim 5, wherein the microbial strain belonging to species *Zopfiella curvata* is *Zopfiella curvata* No. 37-3.

7. *Zopfiella curvata* No. 37-3 strain having the characteristics of BP-4369.

* * * * *